United States Patent [19]

Gaffar et al.

[11] Patent Number: 5,002,759

[45] Date of Patent: Mar. 26, 1991

[54] OLIGOSACCHARIDE INHIBITION OF *STREPTOCOCCUS PYOGENES* ADHESION

[75] Inventors: Abdul Gaffar, Princeton, N.J.; Ronald J. Gibbons, Boston, Mass.; Stanislawa Tylewksa, Warsaw, Poland

[73] Assignees: Colgate-Palmolive Company, Piscataway, N.J.; Forsyth Dental Center, Boston, Mass.

[21] Appl. No.: 384,446

[22] Filed: Jul. 25, 1989

[51] Int. Cl.$^5$ .......................... A61K 7/16; A61K 9/68
[52] U.S. Cl. ........................................ 424/49; 424/48; 424/440; 424/441; 426/3; 426/660; 514/54
[58] Field of Search ...................... 514/54; 426/3, 660; 424/48, 49, 440, 441

[56] References Cited

U.S. PATENT DOCUMENTS

| | | |
|---|---|---|
| 2,333,950 | 11/1943 | Olsen et al. |
| 4,029,760 | 6/1977 | De Roeck ........................... 514/54 |
| 4,282,204 | 8/1981 | Phillips et al. ........................ 514/54 |
| 4,287,173 | 9/1981 | Carlo et al. ........................... 514/54 |
| 4,316,894 | 2/1982 | Omoto et al. ........................ 435/169 |
| 4,357,326 | 11/1982 | Nair et al. ............................. 514/54 |
| 4,457,921 | 7/1984 | Stroz et al. |
| 4,464,360 | 8/1984 | Leffler et al. |
| 4,661,345 | 4/1987 | Tuomanen |
| 4,665,060 | 5/1987 | Mardh et al. |
| 4,695,326 | 9/1987 | Takazoe et al. ...................... 514/54 |
| 4,789,735 | 12/1988 | Frank et al. ........................... 514/54 |
| 4,818,817 | 4/1989 | Shoham et al. ...................... 514/54 |
| 4,859,656 | 8/1989 | Kjelleberg et al. ................... 514/54 |
| 4,859,656 | 5/1989 | Sugden ................................ 514/54 |
| 4,895,838 | 1/1990 | McCluer et al. ..................... 514/54 |

FOREIGN PATENT DOCUMENTS

| | | |
|---|---|---|
| 0240098 | 10/1987 | European Pat. Off. |
| 2019406 | 10/1979 | United Kingdom. |
| 2165451 | 4/1986 | United Kingdom. |
| 2182558 | 5/1987 | United Kingdom. |
| 2183438 | 6/1987 | United Kingdom. |

OTHER PUBLICATIONS

Cassels, F. J. et al., Derwent Abstract WPIACC. No. 89-339704146 (8-29-89 of U.S. Appln. Ser. No. 07/349,772 (5-10-89) Olgiosaccharide from Cell Walls of *Streptococcus sanguishi* for Inhibiting or Reversing Build Up of Human Dental Plaque.

The Article by Wadström et al., published in Current Microbiology, vol. 7, (1982), pp. 343-346 entitled: *Glycoconjugates as Possible Receptors for Streptococcus pyogenes.*

The Article by Ellen et al., published in the Infection and Immunity, May 1972, pp. 826-830 entitled: M Protein-Associated Adherence of *Streptococcus pyogenes* to Epithelial Surfaces Prerequisite for Virulence.

The Article by Tylewska et al., published in Current Microbiology, vol. 16, (1987), pp. 129-135 entitled: Application of Percoll Density Gradients in Studies of the Adhesion of *Streptococcus pyogenes* to Human Epithelial Cells.

The Article by Tylewska et al., published in Current Microbiology, vol. 16, (1988), pp. 209-216, entitled: Binding Selectivity of *Streptococcus pyogenes* and M--protein to Epithelial Cells Differs from that of Lipoteichoic Acid.

The Article by Beachey published in the Journal of Infectious Disease, vol. 143, No. 3, Mar. 1981, pp. 325-345 entitled: Bacterial Adherence: Adhesion-Receptor Interactions Mediating the Attachment of Bacteria to Mucosal Surfaces.

*Primary Examiner*—Shep K. Rose
*Attorney, Agent, or Firm*—Robert Sullivan; Murray Grill; Robert Stone

[57] ABSTRACT

A method of, and oral composition for, inhibiting adherence of *Streptococcus pyogenes* to pharyngeal and oral mucosa cells by treating these cells with an oligosaccharide having at least one fucose moiety or a galactose moiety which is free of digalactose and N-acetylneuraminyl lactose.

10 Claims, No Drawings

OLIGOSACCHARIDE INHIBITION OF STREPTOCOCCUS PYOGENES ADHESION

FIELD OF THE INVENTION

This invention relates to a method of inhibiting adherence and promoting desorption of Streptococcus pyogenes to pharyngeal and oral mucosa cells by treating these cells with an oligosaccharide.

SUMMARY OF THE INVENTION

The object of this invention is to inhibit the attachment of Streptococcus pyogenes to human epithelial cells by treating pharyngeal and oral mucosal cells with an oligosaccharide.

Another object of the invention is to incorporate an adhesion inhibiting oligosaccharide into a preparation for oral application.

Conventional therapy for S. pyogenes infections has mainly consisted of treatment with antibiotics such as penicillin and tetracycline. Unfortunately, antibiotics such as penicillin and tetracycline exhibit broad spectrum antimicrobial activity. Thus, treatment with these antibiotics tends to kill not only S. pyogenes but a number of other bacterial species, some of which may actually be beneficial to the body. In contrast, the present invention, by using oligosaccharides to specifically inhibit the adherence of S. pyogenes to pharyngeal and oral mucosal cells, does not disturb the normal microbial ecology of the mouth. Further, many oligosaccharides are derived from natural sources which are endogenous, and therefore unlikely to be, distruptive to the body.

BACKGROUND OF THE INVENTION

Adherence is an important early event in the pathogenesis of bacterial infections in animals and humans. Studies have shown that the infectious ability of bacteria is related to the ability of bacteria to adhere to host cells. In the first stages of infection, bacterial adhesins, adhesive molecules on the surface of bacteria, bind to receptor materials on the host cell membrane.

Surprisingly, it has been found that the adherence of a bacterium such as Streptococcus pyogenes to human epithelial pharangeal and oral mucosal cells can be inhibited by oligosaccharides. Streptococcus Pyogenes, a group A beta hemolytic streptococci which causes pharyngitis, exhibits tissue tropism, i.e. it is virtually found only in humans.

Early studies by Ellen and Gibbons (Infection and Immunity, pp. 826-830 May 1972) indicated that M protein functions in the attachment of S. pyogenes to epithelial surfaces. On the other hand, subsequent studies by Beachey (J. of Infectious Diseases 143(3), pp. 325-345(1981)) indicated that attachment of S pyogenes to host receptor cells occurred through fatty acid ends of lipoteichoic acid molecules on the S. pyogenes surface interacting with host cell membrane receptors. More recently Tylewska et al (Current Microbiology,16, pp. 209-216(1988)) have confirmed that the M protein in the S. pyogenes cell membrane may play an important role in S. pyogenes adhesion to host cell membranes. While the inventors do not wish to be bound to any one theory, it is believed that inhibition by oligosaccharide of the adherence of S. pyogenes to human pharyngeal and oral mucosal cells may be accomplished by the oligosaccharide effectively mimicing the host cell receptors for M protein, thus preventing binding of S. pyogenes to the receptors of M protein on the host cell membrane.

DETAILED DESCRIPTION

The present invention relates to the inhibition of S. pyogenes adhesion to human pharyngeal and oral mucosal cells by oligosaccharides.

The oligosaccharide contains two or more, preferably 3 or more sugar residues, at least one of which is a galactose moiety free of digalactose and N-acetylneuraminyl lactose, or a fucose moiety. It presently appears that the exact linkage between the galactose moiety or fucose moiety and other sugar residues does not affect the utility of the oligosaccharides of the invention.

Preferred oligosaccharides include:

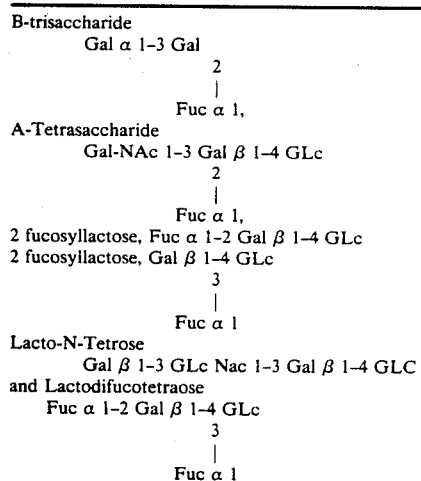

The effect of oligosaccharides on the adhesion of S. pyogenes to human epithelial pharyngeal and oral mucosal cells of S. pyogenes is determined according to the following method. Epithelial cells are obtained by gently scraping the pharangeal, buccal or tongue mucosal surfaces of healthy adults. The cells are suspended in 0.01M phosphate buffer (pH 7.2) containing 0.1% bovine serum albumin (BSA) and washed twice by centrifugation. The suspension is adjusted to contain approximately $5 \times 10^5$ cells/ml. The attachment of S. pyogenes to the epithelial cells is determined by admixing $^3$H-labelled S. pyogenes with the epithelial cells. The mixture is then centrifuged in the presence of Percoll, a colloidal Polyvinylpyrrolidone coated silica (available from Sigma Chemical Corporation) to form a density gradient. Under these conditions, epithelial cells with attached bacteria form a tight band near the top of the centrifuge tube while unattached streptococci form a band near the bottom. The number of bacteria associated with epithelial cells is determined by direct scintillation counting.

Various oligosaccharides were added to the S. pyogenes epithelial cell mixture. The measured decrease in relative absorption of S. pyogenes in the presence of oligosaccharide is shown in the following table.

TABLE

| Control | Concentration mg/ml | Relative Adsorption % |
|---|---|---|
| (.01M Phosphate Buffer/BSA pH = 7.2 | — | 100 |

TABLE-continued

| Control | Concentration mg/ml | Relative Adsorption % |
| --- | --- | --- |
| Lacto-N-tetraose | 0.5 | 55 |
| Lactodifucotetraose | 0.5 | 54 |
| B-Trisaccharide | 0.25 | 60 |
| A-Tetrasaccharide | 0.25 | 62 |
| 3-fucosyllactose | 0.5 | 56 |

These results show that the adherence of *S. pyogenes* to epithelial pharangeal, buccal, or tongue mucosal surfaces is significantly inhibited by oligosaccharides.

Preparations containing oligosaccharides for oral application may be in any convenient form, such as a mouthrinse, tablet or lozenge, chewing gum, throat spray and the like. The oral application may also be in the form of elixirs, syrups or suspensions, for example, solutions containing 0.1 to 5% by weight oligosaccharide, sugar and a mixture of ethanol, water, glycerol, propylene glycol and optionally aroma, saccharine and-/or sodium carboxymethylcellulose as a dispersing agent.

A mouthrinse or mouthwash may be prepared by mixing a nontoxic alcohol and water vehicle with flavoring oil, nonionic surfactant, humectant, sweetener, color and optionally antibacterial antiplaque agent, for example, cetyl pyridinium chloride, benzethonium chloride, and chlorhexidine.

The alcohol component of a mouthwash, typically present in an amount of about 5-25% by weight, is a nontoxic alcohol such as isopropanol or ethanol, preferably utilizing denaturing components which also function as flavoring agents. These flavoring agents are used in an amount between about 1% and 2% of the total alcohol content of the mouthwash. Water typically comprises at least about 50% by weight of a mouthrinse and humectant about 5-40% by weight. Generally, the ratio of water to alcohol is in the range of from about 1:1 to about 20:1 preferably from 3:1 to 20:1 and most preferably from about 5:1 to 10:1 by weight. The total amount of water-alcohol mixture in this type of preparation is typically in the range of from about 70 to about 99.9% by weight of the preparation.

The mouthwash may also contain 0.5 to 5% of a water-soluble organic surfactant, typically an amphoteric surfactant such as betaine, and most preferably a nonionic surfactant. Preferable nonionic surfactants include condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate), and most preferably polypropyleneoxide (e.g. Pluronic materials).

Examples of mouthwash formulations which may be employed in the method of the present invention are as follows:

| | parts by weight |
| --- | --- |
| ethyl alcohol | 10.0 |
| glycerol | 10.0 |
| flavor | 0.4 |
| sodium saccharin | 0.03 |
| nonionic surfactant | 2.0 |
| oligosaccharide | 0.1 to 5.0 |
| water | Q.S. to 100 |

The oligosaccharids of this invention can also be incorporated in lozenges or in chewing gum or other products, e.g. by stirring into a warm gum base or coating the outer surface of a gum base; illustrative of which may be mentioned jelutone, rubber latex, vinylite resins, etc., desirably with conventional filler materials such as plasticizers or softeners, sugar or other sweeteners or carbohydrates such as glucose, sorbitol, sorbitol syrup, mannitol, xylitol, hydrogenated starch hydrolysate, and the like, and artificial sweeteners for example, aspartame and L-aspartic acid derived sweeteners, saccharin salts, acesulfame-K and the like, and the free acid form of saccharin, and protein based sweeteners such as thaumatin.

A typical chewing gum may contain the following ingredients, in percent by weight based on the weight of the total gum formulation:

| Ingredients | parts by weight |
| --- | --- |
| Gum base | 10-40 |
| Sucrose | 50-75 |
| Corn syrup or Glucose | 10-20 |
| Oligosaccharide | 0.01 to 5 |
| Flavor | 0.1-5 |

An alternate chewing gum formulation is as follows:

| Ingredients | parts by weight |
| --- | --- |
| Gum base | 10-50 |
| Binder | 3-10 |
| Filler (Sorbitol, mannitol or combination thereof) | 5-80 |
| oligosaccharide | 0.01 to 5 |
| Flavor | 0.1-5 |

In certain sugarless gums, there is used as the binder ingredient a solution of sorbitol in water containing from about 10% to about 80%, preferably from about 50% to about 75% by weight of sorbitol in $H_2O$. In others, there is used a gum acacia-in-water system containing from about 30% to about 60%, preferably from about 45% to about 50% by weight of gum acacia powder.

The ingredient referred to heretofore in the formulations simply as "gum base" is susceptible to many variations. In general, a gum base is prepared by heating and blending various ingredients, such as natural gums, synthetic resins, waxes, plasticizers, etc. in a manner well known in the art. Typical examples of the ingredients found in a chewing gum base are masticatory substances of vegetable origin, such as chicle, crown gum, nispero, rosidinha, jelutong, pendare, perillo, niger gutta, tunu, etc.; masticatory substances of synthetic origin such as butadiene-styrene polymer, isobutyleneisoprene copolymer, paraffin, petroleum wax, polyethylene, polyisobutylene, polyvinylacetate, etc.

A variety of traditional ingredients may be incorporated in the gum base, such as plasticizers of softeners.

Examples of these ingredients include lanolin, stearic acid, sodium stearate, potassium stearate, glyceryl triacetate, glycerine, lecithin, glyceryl monostearate and the like. Natural waxes, petroleum waxes, polyurethyane waxes, paraffin waxes and microcrystalline waxes may also be incorporated into the gum base to obtain a variety of desirable textures and consistency properties. Mixtures of these traditional ingredients are also contemplated. These traditional ingredients are generally employed in amounts of up to about 30% by weight, and preferably, in amounts of from about 3% to about 20% by weight of the final chewing gum product.

Mineral fillers may include aluminum hydroxide, alumina, aluminum silicate, titanium dioxide, talc, calcium carbonate, tricalcium phosphate, and mixtures thereof.

The flavoring which can be included in the chewing gum compositions made according to this invention can comprise one or more natural and/or synthetic flavors and/or oils derived from plants, leaves, flowers and fruit. Representative flavors and oils of these types include acids such as adipic, succinic and fumaric acid; citrus oils cuch as lemon oil, orange oil, lime oil and grapefruit oil; fruit essences, such as apple essence, pear essence, peach essence, strawberry essence, apricot essence, raspberry essence, cherry essence, plum essence and pineapple essence; essential oils cuch as peppermint oil, spearmint oil, bay oil, anise oil, oil of nutmeg, oil of sage, oil of bitter almonds, cassia oil and methylsalicylate (oil of wintergreen). Various synthetic flavors, such as those for a mixed fruit, may also be incorporated in the chewing gum with or without conventional preservatives.

The vehicle or carrier in a tablet or lozenge is a non-cariogenic solid water soluble polyhydric alcohol (polyol) such as mannitol, xylitol, sorbitol, maltitol, a hydrogenated starch hydrolysate, for example Lycasin, hydrogenated disaccharides and hydrogenated polysaccharides, in an amount of about 90-98% by weight of the total composition. Solid salts such as sodium bicarbonate, sodium chloride, potassium bicarbonate or potassium chloride may totally or partially replace the polyol carrier.

Tableting lubricants, in minor amounts of about 0.1 to 5% by weight, may be incorporated into the tablet or lozenge formulation to facilitate the preparation of both the tablets and lozenges. Suitable lubricants include vegetable oils such as coconut oil, magnesium stearate, aluminum stearate, talc, starch and Carbowax Lozenge formulations may contain about 2% gum as barrier agent to provide a shiny surface as opposed to a tablet which has a smooth finish Suitable non-cariogenic gums include polycarboxylates such as Kappa carrageenan, carboxymethyl cellulose, hydroxyethyl cellulose, Gantrez and the like.

The lozenge or tablet may optionally be coated with a coating material such as wax, shellac, sodium carboxymethyl cellulose, polyethylene/maleic anhydride copolymer or kappacarrageenan to further increase the time it takes the tablet or lozenge to dissolve in the mouth. The uncoated tablet or lozenge is slow dissolving, providing a sustained release rate of active ingredients of about 3 to 5 minutes. Accordingly, the solid dose tablet and lozenge composition of this invention affords a relatively longer time period of contact with the active ingredients.

Examples of lozenge formulations which may be employed in the method of the present invention are as follows:

|  | parts by weight |
|---|---|
| Sorbitol | 75–98 |
| Corn Syrup | 1–20 |
| Flavor Oil | 0.1–1.0 |
| Tablet Lubricant | 0.1–5.0 |
| Oligosaccharide | 0.01–5 |
| Water | 0.01–0.2 |

Various other materials may be incorporated in the oral preparations of this invention such as whitening agents, preservatives, for example phenol, thymol, methyl salicylate, hexylresorcenol, silicones, chlorophyll compounds, anticalculus agents and/or ammoniated material such as urea diammonium phosphate, and mixtures thereof. These adjuvants, where present, are incorporated in the preparations in amounts which do not substantially adversely affect the properties and characteristics desired.

Any suitable flavoring of sweetening material may also be employed. Examples of suitable flavoring constituents are flavoring oils, e.g. oil of spearmint, peppermint, wintergreen, sassafras, clove, sage, eucalyptus, marjoram, cinnamon, lemon and orange, and methyl salicylate. Suitable sweetening agents include sucrose, lactose, maltose, sorbitol, xylitol, sodium cyclamate, perillartine, APM(aspartyl phenyl alanine, methyl ester), sodium saccharine and the like. Suitably, flavor and sweetening agents may together comprise from about 0.1% to 5% more of the preparation.

The following examples are further illustrative of the nature of the present invention, but it is understood that the invention is not limited thereto. All amounts and proportions referred to herein and in the appended claims are by weight and temperatures are in degrees C unless otherwise indicated.

Example 1

Mouthrinse

| Ingredient | Mouthrinse Weight % |
|---|---|
| Ethyl Alcohol | 10.0 |
| Glycerol | 10.0 |
| Flavor | 0.4 |
| Sodium Saccharin | 0.03 |
| Pluronic F 108 | 2.0 |
| Cetyl Pyridinium Chloride | 0.05 |
| Lactodifucotetraose | .1 |
| Water | Q.S. to 100 |

A mouthrinse composition is prepared according to Example 1. Pluronic F 108 is a nonionic surfactant block copolymer of polyoxyethylene and polyoxypropylene. The mouthrinse is introduced into the oral cavity and mixed therethrough thereby reducing adherence of S. pyogenes to epithelial pharyngeal and oral cells.

Example 2

| Ingredient | Lozenge Weight % |
|---|---|
| Sorbitol | 97.2 |
| Corn Syrup | 2 |

-continued

| Lozenge | |
| --- | --- |
| Ingredient | Weight % |
| Flavor Oil | 0.5 |
| Magnesium Stearate | 0.15 |
| Lactodifucotetraose | 0.1 |
| Water q.s | 0.05 |

A lozenge composition is prepared according to Example 2. The lozenge is intoduced into the oral cavity and dissolved there, thereby reducing adherence of S. pyogenes to epithelial pharyngeal and oral cells.

Example 3

Chewing Gum

| Chewing Gum | |
| --- | --- |
| Ingredients | Parts by weight |
| Gum Base | 30.0 |
| Sorbitol | 42.5 |
| Mannitol | 4.0 |
| 70% Sorbitol in H$_2$O | 16.5 |
| Glycerin | 5.0 |
| Lactodifucotetraose | 0.25 |
| Flavoring | q.s. 100 |

A chewing gum composition is prepared according to Example 3. The chewing gum composition is introduced into the oral cavity and masticated thereby reducing adherence of S. pyogenes to epithelial pharyngeal and oral cells.

Example 4

Chewing Gum

| Chewing Gum | |
| --- | --- |
| Ingredients | parts by weight |
| Gum Base | 25.00 |
| Lecithin | .5 |
| Softeners | 9.6 |
| Mannitol | 15.00 |
| Flavor | 2.6 |
| Lactodifucotetraose | 0.35 |
| Sorbitol | 46.95 |
| | 100.00 |

A chewing gum composition is prepared according to Example 4. The chewing gum composition is introduced into the oral cavity and masticated thereby reducing adherence of S. pyogenes to epithelial pharyngeal and oral cells.

The above chewing gum formulations are exemplary only. Many additional formulations are described in the prior art, and in carrying out this invention, such formulations can be employed.

We claim:

1. A method of inhibiting adherence of Streptococcus pyogenes to epithelial pharyngeal and oral cells comprising preparing a formulation containing an oligosaccharide containing at least one fucose moiety or a galactose moiety which is free of N-acetylneuraminyl lactose and contacting said cells in the oral cavity with said formulation.

2. A method of inhibiting adherence to epithelial pharyngeal and oral cells as in claim 1 wherein said oligosaccharide contains at least one fucose moiety.

3. A method of inhibiting adherence to epithelial pharyngeal and oral cells as in claim 1 wherein said oligosaccharide contains at least one galactose moiety free from digalactose and n-acetylneuraminyl lactose.

4. A method of inhibiting adherence to epithelial pharyngeal and oral cells as in claim 2 wherein said oligosaccharide is selected from the group consisting of B trisaccharide, A tetrasaccharide, fucosyllactose, and lactodifucotetraose.

5. A method of inhibiting adherence to epithelial pharyngeal and oral cells as in claim 3 wherein said oligosaccharide is lacto-N-tetrose.

6. A mouthrinse composition for inhibiting adherence of Streptococcus pyogenes to epithelial pharyngeal and oral cells comprising 0.1 to 5.0% by weight of an oligosaccharide containing at least one fucose moiety or a galactose moiety which is free from digalactose and n-acetylneuraminyl lactose in a vehicle comprising a non-toxic alcohol and water.

7. A mouthrinse composition as in claim 6 wherein said oligosaccharide contains at least one fucose moiety.

8. A mouthrinse composition as in claim 6 wherein said oligosaccharide contains at least one galactose moiety free from digalactose and n-acetylneuraminyl lactose.

9. A mouthrinse composition according to claim 7 wherein said oligosaccharide is selected from the group consisting of B trisaccharide, A tetrasaccharide, fucosyllactose, and lactodidifucotetraose.

10. A mouthrinse composition as in claim 8 wherein said oligosaccharide is lacto-N-tetrose.

* * * * *